United States Patent [19]
Gooberman et al.

[11] Patent Number: 5,789,411
[45] Date of Patent: Aug. 4, 1998

[54] IMPROVEMENTS TO RAPID OPIOID DETOXIFICATION

[75] Inventors: Lance L. Gooberman, Haddonfield, N.J.; Colin Brewer, London, United Kingdom

[73] Assignee: Lance L. Gooberman P. C., Centerville, N.J.

[21] Appl. No.: 660,528

[22] Filed: Jun. 17, 1996

Related U.S. Application Data

[63] Continuation-in-part of Ser. No. 526,429, Sep. 11, 1995.
[51] Int. Cl.$^6$ .......................... A61K 31/44; A61K 31/495
[52] U.S. Cl. .......................... 514/255; 514/282; 514/812
[58] Field of Search .......................... 514/255, 282, 514/812

[56] References Cited

U.S. PATENT DOCUMENTS 5,272,149  12/1993  Stalling .................................. 514/255

OTHER PUBLICATIONS

Alim, T.N. et al., "Tolerability Study of a Depot Study Form of Naltrexone Substance Abusers", *Problems of Drug Dependence, 1994: Proceedimgs of the 56th Annual Scientific Meeting, The College on Problems of Drug Dependence, Inc.*, vol. II: Abstracts, NIDA Research Monograph 153, p. 253, U.S. Department of Health and Human Services, National Institute on Drug Abuse, Rockville, MD, 1995.

Chiang, C.N. et al., "Kinetics of a Naltrexone Sustained-Release Preparation", *Clin. Pharmacol. Ther.*, vol. 36, No. 5, pp. 704–708, Nov. 1984.

Wall, Monroe E. et al., "Metabolism and Disposition of Naltrexone in Man After Oral and Intravenous Administration", *Metabolism and Disposition*, vol. 9, No. 4, pp. 369–375, 1981.

Renault, Pierre F., "Treatment of Heroin–Dependent Persons With Antagonists: Current Status", *Naltrexone: Research Monograph 28*, pp. 11–22, National Institute on Drug Abuse, 1980.

Wall, Monroe E. et al., "Naltrexone Disposition in Man After Subcutaneous Administration", *Metabolism and Disposition*, vol. 12, No. 6, pp. 677, 679, & 682, 1984.

Reuning, R.H. et al., "Pharmacokinetic Quantitation of Naltrexone Controlled Release From a Copolymer Delivery System", *Journal of Pharmacokinetics and Biopharmaceutics*, vol. 11, No. 4, pp. 369–387, Plenum Publishing Corporation, 1983.

Sharon, A. Carl et al., "Development of Drug Delivery Systems for Use in Treatment of Narcotic Addiction", *Naltrexone: Research Monograph 28*, pp. 194–213, National Institute On Drug Abuse, 1980.

Misra, Anand L., "Current Status of Preclinical Research on Disposition, Pharmacokinetics, and Metabolism of Naltrexone", *Naltrexone: Research Monograph 28*, pp. 132–146, National Institute on Drug Abuse, 1980.

Harrigan, Stephen E., "Pharmacological Evaluation of Narcotic Antagonist Delivery Systems in Rhesus Monkeys", *Naltrexone: Research Monograph 28*, pp. 77–92, National Institute on Drug Abuse, 1980.

Affidavit of Juan Jose Legarda, 1995.

Affidavit of Norbert Loimer, 1995.

Forrester-Sigma, Patrick et al., "A New Assault On Addiction", *Newsweek*, Jan. 30, 1995.

Loimer, Norbert et al., "Combined Naloxone/Methadone Preparations for Opiate Substitution Therapy", *Journal of Substance Abuse Treatment*, vol. 8, pp. 157–160, 1991.

Loimer, Norbert et al., "Similar Efficacy of Abrupt and Gradual Opiate Detoxification", *American Journal of Drug and Alcohol Abuse*, 17(3), pp. 307–312, 1991.

Bastin, Richard, "New drug cure gives addicts painless cold turkey", Reuters, Limited, 1994.

Abstract of O'Connor, PG et al., "Ambulatory opiate detoxification and primary care", *J. Gen. Intern, Med.*, 7(5) : 532–4, Sep.–Oct. 1992.

Abstract of Senft, RA, "Experience with clonidine–naltrexone for rapid opiate detoxification", *J. Subst. Abuse Treat.*, 8(4); 257–9, 1991.

Abstract of Fraser, AD, "Clinical toxicology of drugs used in the treatment of opiate dependency", *Clin. Lab. Med.*, 10(2):375–86, Jun. 1990.

Nutt, David J., "Pharmacological Mechanism of Benzodiazepine Withdrawal", The Reckitt and Colman Psycopharmacology Unit, The Medical School, Bristol, England, undated.

Article entitled "Is RO 15–4513 A Specific Alcohol Antagonist", undated.

Jordan, C. et al., Respiratory Depression Following Diazepam: (Reversal with High–Dose Naloxone), *The American Society of Anesthesiologists, Inc.*, 53:293–298, 1980.

Loimer, Norbert et al., "Technique for Greatly Shortening The Transition From Methadone To Naltrexone Maintenance of Patients Addicted to Opiates", *American Journal of Psychiatry*, Clinical and Research Reports 148–7, pp. 993–935, Jul. 1991.

Loimer, N. et al., "Continuous Naloxone Administration Suppresses Opiate Withdrawal Symptoms in Human Opiate Addicts During Detoxification Treatment", *Journal of Psychiatry*, Res. vol. 23, No. 1, pp. 81–86, 1989.

Eisenberg, Richard, "Effects of Chronic Treatment with Diazepam, Phenobarbital, Or Amphetamine on Naloxone–Precipitated Morphine Withdrawal", *Drug and Alcohol Dependence*, 15, pp. 375–381, 1985.

(List continued on next page.)

*Primary Examiner*—James H. Reamer
*Attorney, Agent, or Firm*—Duane, Morris & Heckscher LLP

[57] ABSTRACT

Rapid opioid detoxification procedures are provided which include sedating a patient with an anesthetic agent having a short full recovery period. The patient is administered an opioid antagonist while sedated and can be revived to an ambulatory condition within eight hours of initiating therapy. The described methods for detoxification also include administering a diarrhea suppressant, such as octreotide acetate, to limit this unfortunate side effect of the detoxification.

29 Claims, No Drawings

OTHER PUBLICATIONS

Presslich, Otto et al., "Opiate Detoxification Under General Anesthesia By Large Doses of Naloxone", *Clinical Toxicology*, 27(4&5), pp. 263–270, 1989.
Abstract of U.S. Patent No. 5,173,287 to Smith.
Abstract of U.S. Patent No. 5,075,341 to Mendelson et al.
Abstract of U.S. Patent No. 5,069,909 to Roos et al.
Abstract of U.S. Patent No. 5,389,670 to Fontana.
Abstract of U.S. Patent No. 5,370,681 to Herweck.
Abstract of U.S. Patent No. 5,316,938 to Keen et al.
Abstract of U.S. Patent No. 5,288,488 to Backman et al.
Abstract of U.S. Patent No. 5,286,718 to Elliott.
Abstract of U.S Patent No. 5,268,463 to Jefferson.
Abstract of U.S. Patent No. 5,243,094 to Borg.
Abstract of U.S. Patent No. 5,223,605 to Fanslow et al.
Abstract of U.S. Patent No. 5,212,072 to Blalock et al.
Abstract of U.S. Patent No. 5,189,064 to Blum et al.
Abstract of U.S. Patent No. 5,173,486 to Monkovic et al.
Abstract of U.S. Patent No. 5,137,712 to Kask et al.
Abstract of U.S. Patent No. 5,128,145 to Edgren et al.
Abstract of U.S. Patent No. 5,120,543 to Hagin et al.
Abstract of U.S. Patent No. 5,110,364 to Mazur et al.
Abstract of U.S. Patent No. 5,108,927 to Dorn.
Abstract of U.S. Patent No. 5,091,180 to Walker et al.
Abstract of U.S. Patent No. 5,084,377 to Rowan.
Abstract of U.S. Patent No. 5,077,195 to Blalock et al.
Abstract of U.S. Patent No. 5,070,014 to Dorn.
Abstract of U.S. Patent No. 5,057,321 to Edgren et al.
Abstract of U.S. Patent No. 5,043,163 to Pap et al.
Abstract of U.S. Patent No. 5,034,416 to Smith.
Abstract of U.S. Patent No. 5,026,728 to Kendall et al.
Abstract of U.S. Patent No. 5,021,236 to Gries et al.
Abstract of U.S. Patent No. 5,013,539 to Morris et al.
Abstract of U.S. Patent No. 4,997,454 to Violante et al.
Abstract of U.S. Patent No. 4,952,376 to Peterson.
Abstract of U.S. Patent No. 4,935,428 to Lewis.
Abstract of U.S. Patent No. 4,920,044 to Bretan, Jr.
Abstract of U.S. Patent No. 4,897,246 to Peterson.
Jeffrey, Glenn, "Rapid Opioid Detox with Naltrexone: Its Evolution, Its Neurophysiology and Further Pharmocologic Considerations", pp. 1–51, Cornell University Medical Center, undated.
Legarda, Juan Jose, "A Twenty–four Inpatient Detoxification Treatment for Heroin Addicts: A Preliminary Investigation", *Drug and Alcohol Dependence*, 35, pp. 91–93, 1994.
Letter from Eva Clifton to Lance Gooberman dated May 13, 1995.
Trade Literature from Krakauers Ltd. dated May 14, 1995.

IMPROVEMENTS TO RAPID OPIOID DETOXIFICATION

RELATED APPLICATIONS

This application is a continuation-in-part application of U.S. patent application Ser. No. 08/526,429, dated Sep. 11, 1995 now pending, and entitled "Rapid Opioid Detoxification."

FIELD OF THE INVENTION

This invention relates to methods of rapidly detoxifying opioid addicts so as to relieve conscious symptoms, and more particularly, to methods of detoxification employing sedation and a narcotic antagonist while permitting the patient to be ambulatory within eight hours of beginning treatment.

BACKGROUND OF THE INVENTION

Heroin addiction is a growing healthcare problem in the United States. The United States Department of Health and Human Services' Substance Abuse Branch issued a report in December of 1994 stating that the number of emergency department visits directly related to heroin use rose from 48,000 in 1992 to 63,000 in 1993, a 31% increase. The rate of heroin-related episodes per 100,000 people rose 81%, from 15 to 28 per 100,000, between 1990 and 1993. Upon breaking down the heroin-using population into ethnic groups and age groups, it has been demonstrated that all subsets have increased rates of use for this time period.

Human opiate detoxification has been in use for some time. More than 31,000 individuals of the Empire Blue Cross and Blue Shield subscriber base in New York were hospitalized at least once for opiate dependency between 1982 and 1992. The majority of these individuals were working adults, and their principal reason for hospitalization was addiction treatment. Drug detoxification accounted for 96% of the admissions, and the length of stay ranged between five and ten days.

It is widely known that heroin addicts fear and loathe heroin detoxification. For the addict, withdrawal can be like having a massive panic attack, an acute case of Huntington's Chorea, a psychological shock syndrome, and a nasty flu, all rolled into one.

Even if we discount the less than warm reception by addicts, the current method of detoxifying an individual from opiates is flawed in several respects. First of all, it is extremely uncomfortable for individual patients. Second, it can take days, and even weeks, for treatment, and this treatment is very expensive when one considers the overall length of stay at a hospital. Third, it is not very effective. Early relapse is the rule rather than the exception.

In the 1980s, outpatient protocols were developed in an attempt to reduce expenses and to entice more addicts to receive treatment. In one particular therapy, a shortened five-day schedule was employed. On the first day, patients received a naloxone hydrochloride ("naloxone") challenge test at 9:00 a.m., using 0.8 mgs of naloxone, and then were started on clonidine hydrochloride ("clonidine") premedication. Clonidine is a potent antihypertensive agent and stimulates adrenergic receptors in the brain, leading to reduced sympathetic nervous system output. Daily averages of medication were, for day two: clonidine 1.1 mgs and naltrexone 8 mgs; day three: clonidine 0.6 mgs and naltrexone 40 mgs; day four: clonidine 0.3 mgs and naltrexone 50 mgs; and day five: clonidine 0.2 mgs and naltrexone 150 mgs.

In 1988, Loimer et al. described an inpatient technique in which 12 hours after the patient's last dose of opiate, they were sedated with 100 mgs of the barbiturate, methohexitone. This was followed by further injections of 400 mgs of methohexitone and 10 mgs of naloxone. After the narcotic effect had worn off, 2 mgs of naloxone was given intravenously about 30-40 minutes later. This did not elicit any further withdrawal response. This study showed that the acute onset of withdrawal symptoms induced by naloxone in opiate addicts is blocked by barbiturates.

Loimer et al. in 1991 described another inpatient technique for enabling patients to transfer quickly from methadone to naltrexone maintenance. In a study of seven patients, they induced acute methadone detoxification by using a 4 mg bolus of intravenous naloxone ten minutes after intravenous sedation was started with 30 mgs of midazolam, a short-acting benzodiazepine. After the naloxone infusion was completed, the patients received repeated dosages of flumazenil, a benzodiazepine antagonist, until they were awake. Within hours, the patients tolerated full doses of naltrexone.

Loimer pointed out that conscious sedation with midazolam was safer than general anesthesia. The technique also suppressed withdrawal signs and symptoms. Loimer used intranasal naloxone to induct patients onto naltrexone.

Loimer further described in 1993 an inpatient technique using intranasal naloxone. Twenty opiate-dependent patients reported a mean daily heroin dose of 2.0 grams for at least 2 months prior to detoxification. Twelve hours after their last heroin use, all the patients were sedated with 60 mgs of oral midazolam. Simultaneously, they received 0.3 mgs of clonidine and 5.0 mgs of ondansetron (a selective 5-HT3 receptor antagonist, generally used to prevent nausea and vomiting associated with cancer chemotherapy). Ten minutes later, oral naltrexone, 50 mgs, was administered. The patients typically were asleep fifteen minutes post-midazolam, at which time withdrawal was precipitated by 4 mgs of naloxone administered nasally as a spray. Naltrexone, 50 mgs/day, was continued for the next 2 days before discharge.

Loimer has reported that none of his patients showed severe withdrawal distress before detoxification. He has found that following the administration of naloxone, withdrawal distress was significantly higher than baseline levels at 30, 45, 60 and 90 minutes, but that there were no significant differences from the baseline on all subsequent measurements. Furthermore, he has reported that systolic and diastolic blood pressure and heart rate did not change significantly during treatment.

Legarda and Gossop in 1994 also described an inpatient technique enabling heroin addicts to undergo a rapid transition to naltrexone maintenance, now referred to as rapid opiate detoxification. Legarda belongs to the CITA group, which has been detoxifying heroin patients in Spain, Israel and Mexico under general anesthesia.

As in Loimer et al.'s 1991 report, Legarda and Gossop used intravenous midazolam (0.5-0.7 mgs/kg initially, then as a constant infusion) for sedation. In this study, however, patients received an initial dose of oral naltrexone, 50 mgs, immediately prior to the injection of midazolam, and did not receive any naloxone reversal while under sedation.

They also pretreated the patients with repeated oral doses of guanfacine (like clonidine, a centrally acting agent with alpha-2 agonist properties) 1-2 mgs/hour. Oral doses of loperamide (4 mgs) and ondansetron (8 mgs) were given, to avoid diarrhea and vomiting during the detoxification procedure.

During the time they were sedated, the subjects' opiate withdrawal signs primarily were piloerection, sneezing and motor agitation.

Four hours after the sleep induction, the patients received a naloxone test (0.8 mgs IV), and then 12 hours later they received 50 mgs of naltrexone, both of which provoked no withdrawal responses.

While Dr. Loimer's initial barbiturate procedure has relieved patients of the conscious symptoms of withdrawal by administering general anesthesia simultaneously with a large continuous dose of a pure narcotic antagonist, he requires patients to be carefully monitored for 12 to 24 hours. This is because barbiturate anesthesia tends to accumulate and is not reversible, requiring patients to be watched for an extended period of time following the procedure. It also minimizes the options available to the physician if adverse conditions arise, such as severe respiratory suppression.

The use of the benzodiazepines, such as midazalom is completely reversible by antagonists such as flumazenil, an imidazobenzodiazepine derivative. Flumazenil competitively inhibits the activities at the benzodiazepine recognition site on the brain's receptor complex. Unfortunately, if the patient is dually-addicted to heroin and benzodiazepines, such as Zanax, Halcion, or Valium, the use of flumazenil to reverse the effects of benzodiazepine anesthesia can cause seizures.

In a 1993 Spanish survey of 973 heroin addicts, 68% of the patients admitted to using benzodiazepines, and 43% admitted to using them on a daily basis. It has been observed that heroin-dependent patients often use benzodiazepines in the days and weeks prior to seeking treatment to help them sleep when they are trying to cut down on their own. These reported figures are believed to be conservative since addicts have no trouble concealing their benzodiazepine use from their treating physician, even when provided with a warning of adverse side effects.

The duration of action for flumazenil may also not be sufficient to eliminate the effects of benzodiazepines which are still present in the patient's blood and bile. This can lead to resedation, and requires extended periods of observation. Of course, extended observation is usually associated with additional nights in a hospital and added expense.

Another recent problem that has developed in detoxifying heroin addicts is the occurrence of profuse diarrhea in patients during withdrawal. The problem becomes even more severe when patients are sedated during the procedure, since they have no bowel control.

SUMMARY OF THE INVENTION

Methods of detoxifying patients addicted to one or more opioids are provided by this invention. The methods include sedating the patient with an anesthetic agent, ventilating the sedated patient, administering a diarrhea suppressant to the patient and then detoxifying the patient by injecting an opioid antagonist. The patient is then revived from the effects of the anesthetic and discharged in an ambulatory condition within about eight hours of being sedated. Diarrhea is significantly controlled, preferably with the addition of octreotide acetate solution.

DEFINITIONS naloxone hydrochloride: 1-N-Allyl-7,8-dihydro-14-hydroxymorphinone hydrochloride; a potent antagonist of endorphins and narcotics, including pentazocine; devoid of pharmacologic action when administered without narcotics.

naltrexone: 17-(Cyclopropylmethyl)-4, 5-epoxy-3, 14-dihydroxymorphinan-6-one; an orally active narcotic antagonist; devoid of pharmacologic action when administered in the absence of narcotics.

propofol: an oil-in-water emulsion of 1, 6-diisopropylphenol, a hypnotic with rapid onset and short duration of action; used intravenously for induction and maintenance of general anesthesia. Also called 2, 6-diisopropyl phenol.

octreotide acetate: L-Cysteinamide, D-phenylalanyl-L-cysteinyl-L-phenylalanyl-D-tryptophyl L-Iysyl-L-threonyl-N-[2 hydroxy-I-(hydroxy-methyl) propyl]-, cyclic (2-7)-disulfide; 2[R-(R*,R*)] acetate salt, is a long-acting octapeptide with pharmacologic actions mimicking those of the natural hormone somatostatin. It is commercially available as Sandostatin® octreotide acetate injection, a cyclic octapeptide prepared as a clear sterile solution of octreotide, acetate salt, in buffered sodium chloride for administration by deep subcutaneous (intrafat) or intravenous injection.

opioid: opiates, synthetic narcotics.

opiate: any preparation or derivative of opium, including heroin.

A DETAILED DESCRIPTION OF THE INVENTION

The present invention provides for rapid detoxification of opioid addicts, including those who are dually-addicted to opiates and benzodiazepines.

An outline of the preferred therapy will now be described as an overview. At the initial office visit, a staff member conducts a biopsychosocial interview. At this time, the procedure is explained in depth along with a description of what to expect after detoxification is complete. The importance of group therapy and a support person following therapy is explained to the patient.

A complete history and physical examination is conducted, with a particular attention directed to prior difficulties with anesthesia on the part of the patient or his or her family. In addition, the arms and legs of the patient should be inspected for adequate venous access. An informed consent form is reviewed and executed, and warnings are given concerning what the patient should expect from the procedure.

The sedation procedure preferably involves the use of a rapid sequence induction of anesthesia, in combination with a rapid-acting, intravenous anesthetic agent. Propofol is a preferred rapid-acting intravenous anesthetic agent. Propofol has a half-time of the blood-brain equilibriation of about one to three minutes. Additionally, propofol is known to reverse its effects within minutes. Discontinuation of recommended doses of propofol injection after the maintenance of anesthesia for approximately 1-10 hours results in a prompt decrease in blood propofol concentrations and rapid awakening in less than 20 minutes, and usually within about 10-15 minutes. This is a drastic improvement over barbiturate anesthesia which is known to take hours for complete reversal.

In addition to the induction and sedation agents, the patient is preferably administered a dose of curare and succinylcholine, an effective, inexpensive paralytic agent commonly used in an induction. Paralysis is desirable since it significantly decreases the incidence of vomiting, however, this requires ventilation since it is necessary to breathe for the patient. After paralysis is induced, it can be maintained with pavulon or norcuron until the therapy is complete.

The patient should also be intubated for protecting the airway. When inducing withdrawal in a patient, particularly a severe withdrawal through the use of a narcotic antagonist, vomiting is a frequent side effect. In order to prevent aspiration of this vomitus, with possible life-threatening consequences, a tube can be placed in the airway with an inflated cuff.

After the patient has been intubated and ventilated, a preferred propofol drip is initiated intravenously. The effects of this intravenous anesthetic agent can be completely eliminated merely by discontinuing its administration. This sedative is also safe to use with dually-addicted patients, such as those that have both heroin and benzodiazepine addiction. In the event that adverse pulmonary or respiratory effects occur during detoxification, the patient can be revived nearly immediately. This is not the case with conventional ROD procedures.

In addition to intubation, a nasogastric tube should be inserted into the stomach cavity of the sedated patient. This allows for the insertion of naltrexone, an oral pure narcotic antagonist during the procedure. It also permits the evacuation of the stomach at any time during the procedure, which tends to lessen the production of vomitus should the person regurgitate.

Following sedation and paralysis, the patient is administered an IV of naloxone initially in a dose of at least about 0.4 mgs. This basically initiates withdrawal, typically exhibited by piloerection and a transient elevation of blood pressure. It acts rapidly and is short-acting. Pharmacological antagonism occurs immediately. Evidence of the abstinence syndrome can sometimes be seen, and if any complications arise, the procedure can be abandoned in its early phase.

After withdrawal initiates, the naloxone dosage can be increased to about 12 mgs intravenously, or a smaller dose of a stronger or longer-acting antagonist, such as nalmefene or naltrexone can be administered. This large dose will rapidly strip all of the receptors of opiates.

At about three or four hours, the patient should be fully detoxed, and a maintenance dose of opiate antagonist can be administered. This can be made through oral therapy, for example, by naltrexone, or alternatively, as a subcutaneous injection, implantation or insertion under the skin of the patient with a time-released antagonist-carrier mixture. Preferred carriers could include starch, cellulose or polymeric substances. Such materials should be biodegradable within the human body, and can include, for example, rod-shaped, injectable time-released naltrexone dosages combined with a water soluble glass, or a polymer, such as cross-linked polysiloxane copolymers, ethylene-vinyl acetate, and polyurethanes. See U.S. Pat. Nos. 5,141,748; 5,088,505; 4,957, 119 and 3,887,699, which are hereby incorporated by reference. Such compositions can also include time-release agents, erosion rate modifiers, antimicrobial agents and surfactants. Alternatively, a mechanical device may be used to create a time-lapsed delivery of the preferred long-acting antagonist substances.

The antagonist maintenance therapy preferably continues to release a minimum therapeutic dose at least once every three days, at least for one week following the procedure. This dose should eliminate the mood-altering effects of any opiate that the patient takes, and will help to maintain sobriety while the patient seeks counseling.

The stomach may be evacuated to avoid any vomiting upon awakening the patient. Additional medications, such as cholestyramine or potassium, can be injected to decrease diarrhea or correct electrolyte imbalances. Paralysis is reversed with a known regiment of a paralytic agent antagonist, and the propofol drip is terminated.

Further specific details of the therapy will now be described in the following example.

EXAMPLE I

The patient disrobes and is placed in a hospital bed. A certified registered nurse anesthetist is introduced and reviews the pertinent anesthesia questions with the patient. IV access is established in a peripheral vein with one liter of lactated ringers solution. All subsequent medications will be administered through the intravenous tubing, minimizing needle sticks. A small amount of local anesthetic agent is administered intravenously. The patient is administered 2–3 mg of propofol for the purpose of relaxation. The patient is connected to blood pressure, pulse, pulse oximeter, respiratory, EKG, and end-expiratory $CO_2$ monitoring. (Defibrillator and all emergency drugs are immediately available).

The physician is present throughout the induction and administration of pure narcotic antagonists which is performed in conjunction with the CRNA. A propofol infusion is prepared and accessed to the patient (50 ml vial of 10 mg per ml). Strict aseptic precautions are observed in preparation. A bolus injection of propofol (20 ml via of 10 mg per ml) is prepared and a dose of 2 mg per kg is injected. Simultaneously, the propofol drip is commenced at 100 micrograms per kg per minute (6 mg per kg per hour). The patient is ventilated, intubated and placed on the ventilator. Cricoid pressure is applied during the intubation. Vital signs are recorded every five minutes during induction of anesthesia and every 30 minutes thereafter for the remainder of the procedure. Pavulon 0.1 mg per kg bolus is injected initiating neuromuscular blockade. This facilitates ventilation and prevents vomiting. The patient is then administered Glycopyrrolate 2 mg IV. This atropine-like medication decreases the marked secretions that patients typically produce during withdrawal. An orogastric tube is then placed and the stomach is evacuated. The patient is administered naloxone 0.4 mg IV and observed for signs of withdrawal, i.e., piloerection and increased blood pressure.

Naloxone is used due to its short half-life. It will initiate the withdrawal sufficiently and still allow an opportunity to abandon the procedure even at this point.

The patient is then administered nalmefene 2 mg IV. This drug occupies approximately 50% more of the receptor sites than naloxone and has a longer half-life (10.8 hours).

The patient is then administered naltrexone 50 to 200 mg via the orogastric tube. This initiates the oral therapy with a long-acting agent. Neuromuscular blockade is maintained with norcuron 0.08 to 0.1 mg per kg based upon the patient's response to peripheral nerve stimulation. After three hours, the stomach is again evacuated. Cholestyramine 8 mg is then administered via the orogastric tube. This is for the prevention of diarrhea. At the end of the procedure, approximately 3.5 hours after the induction, the propofol drip is discontinued. The neuromuscular blockage is reversed with neostigmine 2.5 mg and atropine 1 mg IV bolus. This will also decrease abdominal discomfort after the procedure.

The patient is extubated after the following criteria are met: (a) train of four on peripheral nerve stimulation, (b) swallowing, (c) responds appropriately to verbal stimuli, and (d) sustained head lift of six seconds. The OG tube is removed with the endotracheal tube. A medical alert bracelet or necklace is applied to the patient. After about one hour of observation, within which the patient is assisted in getting dressed, he or she is then assisted out to the car. The physician is present at the termination of the procedure and during extubation.

In the post-procedure phase, the patient is very tired, weak and lethargic, and sleep may appear restless accompanied by extensive yawning. Leg and back pains are usually minimal and are relieved by either hot baths or wet/hot compresses. It is essential that the patient take the naltrexone at least once a day, at least for the first week after the procedure. Instructions are again reviewed with the caretaker. Those instructions include what to expect in the post-procedure phase. The caretaker is instructed to call the doctor upon arriving home. The caretaker is provided with the following: 12 capsules containing phenobarbital 250 mg with clonidine 0.25 mg (these medications are administered for the relief of nausea, vomiting, abdominal cramps and insomnia as directed by the physician); one rectal suppository containing phenobarbital 500 mg with clonidine 0.5 mg; and a prescription for naltrexone 50 mg to be taken one daily, dispense 30. The caretaker is instructed to contact the physician upon arrival at home. Contact is then made by telephone between the caretaker and the physician according to the following schedule: every two to three hours on the first day, and every six hours on the second day. Thereafter, contact is made between the patient and/or caretaker and the physician and/or a staff member daily for one week; then every three to four days for one week, followed bi-weekly for two weeks and periodically thereafter.

We give aggressive telephone support to encourage a connection between the patient and a 12-step recovery program. We try to give guidance in obtaining a sponsor and attempt to communicate with the patient's sponsor in order to help facilitate the transition to a support group. Follow-up office visits are scheduled at weekly intervals for two weeks, then bi-monthly for two months, then monthly and as needed thereafter. Again, this is primarily to facilitate the transition to a 12-step recovery program support structure.

EXAMPLE II

The patient disrobes and is placed in a hospital bed, having received a Medical Alert insignia. A certified registered nurse anesthetist performs the pertinent anesthesia history and physical examination.

IV access is established in a peripheral vein with one liter of D5-1/2 lactated Ringers. All subsequent medications will be administered through the intravenous tubing, minimizing needle sticks. A small amount of local anesthetic agent is administered intravenously. The anesthetic agent, Propofol, tends to cause a burning sensation during initial administration and this minimizes discomfort for the patient. The patient is connected to blood pressure, pulse, pulse oximeter, respiratory, EKG, temperature and end-expiratory $CO_2$ monitoring. (Defibrillator and all emergency drugs are immediately available). Intravenous access is establish. The patient is administered 3–5 cc of 1% Lidocaine. This desensitizes the patient's vein prior to the administration of Propofol. The patient is administered 2 mg of Midazolam for its amnestic effect. The patient is administered 20–30 mg of Propofol for the purpose of relaxation and as a test dose. The physician is present throughout the induction and administration of pure narcotic antagonists which are performed in conjunction with the CRNA.

A Propofol infusion is prepared and accessed to the patient (50 ml vial of 10 mg per ml). Strict aseptic precautions are observed in preparation. A bolus injection of Propofol (20 ml vial of 10 mg per ml) is prepared and a dose of 2 mg per kg is injected. Simultaneously, the Propofol drip is commenced at 100 micrograms per kg per minute (6 mg per kg per hour). The patient is ventilated (pre-oxygenation with 100% O2), intubated and placed on the ventilator. Cricoid pressure is applied during the intubation. Vital signs are monitored continuously during intubation and throughout the remainder of the procedure. Pavulon 0.1 mg per kg bolus is injected initiating neuromuscular blockade after adequate airway and ventilation have been established. The patient is then administered Glycopyrrolate 0.2 mg IV. Odansetron 2 mg IV is added. This is an anti-emetic drug which ameliorates the vomiting frequently associated with withdrawal. An octreotide 200 micrograms IV is established. This alleviates the diarrhea and crampy abdominal pain associated with opiate withdrawal. The patient is then administered Naloxone 0.4 mg IV and observed for signs of withdrawal, i.e., piloerection and increased blood pressure. Naloxone is used due to its short half-life. It will initiate the withdrawal sufficiently and still allow an opportunity to abandon the procedure even after withdrawal begins. The patient is then administered Nalmefene 2 mg IV. This drug has a longer half-life (about 10.8 hours) than naloxone. It remains in effect while the oral Naltrexone is being absorbed. An oro-gastric tube is then placed and the stomach is evacuated. The patient is then administered Naltrexone (ReVia) 200 mg via the orogastric tube. This initiates the oral therapy with a long-acting agent. Neuromuscular blockade is maintained with Pavulon based upon the patient's response to peripheral nerve stimulation. After three hours, the stomach is again evacuated. The neuromuscular blockade is reversed with Neostigmine 2.5 mg and Atropine 1 mg IV bolus. At the end of the procedure, approximately 3 hours after the induction, the Propofol drip is discontinued.

The patient is extubated after the following criteria are met: (a) Train of four on peripheral nerve stimulation; (b) Responds appropriately to verbal stimuli; (c) Responds appropriately to verbal stimuli; and (d) Sustained head lift of six seconds. The OG tube is removed. The endotracheal tube is removed. The patient is assisted in getting dressed and out to the car. The physician is present during extubation at the end of the procedure. The patient is then observed for one hour prior to discharge.

In the post-procedure phase, the patient is very tired, weak and lethargic, and sleep may appear restless accompanied by extensive yawning. Leg and back pains are usually minimal and are relieved by either hot baths or hot wet compresses. It is essential that the patient take the Naltrexone (ReVia) at least once a day, at least for the first week after the procedure.

Instructions are again reviewed with the caretaker. Those instructions include what to expect in the post-procedure phase. Telephone numbers are exchanged and verified; these numbers include the physician's office number, beeper number and emergency number. The caretaker is instructed to call the doctor upon arriving home. The caretaker is provided with the following prescriptions: Naltrexone (ReVia) 50 mg to be taken one daily, dispense #30 and refill p.r.n. Clonidine 0.2 mg to be taken one every four hours, dispense #20 with one refill. Octreotide 200 micrograms per ml to be taken one cc subcutaneously q. 12 hours p.r.n. diarrhea; dispense #5 pre-filled syringes with needles. Refill times one.

The caretaker is instructed to contact the physician upon arrival at home. Contact is then made by telephone between the caretaker and the physician according to the following schedule: Every two to four hours on the first day. Every six to twelve hours on the second day. Thereafter, contact is made between the patient and/or caretaker and a doctor or a staff member daily for one week; then every three to four days for one week, then weekly for two weeks and periodically thereafter. We give aggressive telephone support to encourage a connection between the patient and a 12-step recovery program. We try to give guidance in obtaining a sponsor and attempt to communicate with the patient's sponsor in order to help facilitate the transition to a support group.

Patients are evaluated according to the Short Opiate Withdrawal Scale (SOWS) by Michael Gossop during the recovery period, at 24 hours, and at 48 hours. Follow-up office visits are recommended for two weeks, then bi-monthly for two months, then monthly and as needed thereafter. Again, this is primarily to facilitate the transition to a 12-step recovery program support structure.

From the foregoing, it can be realized this invention provides improved rapid opiate detoxification procedures capable of being safely reversed even in the instance where the patient is dually-addicted to benzodiazepines and heroin. The present invention preferably takes advantage of the fast-acting aesthetic ability of propofol, and uses other techniques, such as paralysis, in rendering the detoxification process almost completely without symptoms. Although various embodiments for these therapies have been illustrated, this was for the purpose of describing, but not limiting the invention. Various modifications, which will become apparent to one skilled in the art, fall within the scope of this invention described in the attached claims.

What is claimed is:

1. A method of detoxifying a patient addicted to one or more opioids, comprising:
   sedating said patient with an anesthetic agent;
   administering to said patient a diarrhea suppressant;
   detoxifying said patient by injecting an opioid antagonist into said patient;
   reviving said patient from the effects of said anesthetic agents,
   whereby said patient can be discharged in an ambulatory condition within about eight hours of being sedated with said anesthetic agent without a significant amount of diarrhea.

2. The method of claim 1 wherein said detoxifying step is accomplished within about four hours.

3. The method of claim 1 wherein said anesthetic agent comprises 2,6-diisopropylphenol.

4. The method of claim 1 wherein said opioid antagonist comprises 17-allyl-4, 5 α epoxy-3, 14-dihydroxymorphinan-6-one hydrochloride.

5. The method of claim 1 wherein said diarrhea suppressant comprises octreotide acetate.

6. The method of claim 5 further comprising intubating said patient in order to minimize aspiration of vomitus.

7. The method of claim 6 further comprising administering a long-acting opiate antagonist to said patient.

8. The method of claim 5 further comprising paralyzing said patient with a neuromuscular blocking agent.

9. An opioid detoxification therapy, comprising:
   sedating a patient addicted to an opiate by administering a rapid acting intravenous, anesthetic agent;
   administering a diarrhea suppressant containing an octapeptide with pharmacologic actions mimicking those of a natural hormone, somatostatin,
   intravenously administering a narcotic antagonist containing naloxone hydrochloride to said patient while said patient is sedated to induce withdrawal;
   and reviving said patient by at least terminating an intravenous delivery of said anesthetic agent, whereby said patient remembers little of a plurality of symptoms associated with said withdrawal and experiences little or no diarrhea.

10. The therapy of claim 9 wherein said narcotic antagonist comprises 17-allyl-4, 5 α epoxy-3, 14-dihydroxymorphinan-6-one hydrochloride.

11. The therapy of claim 9 further comprising mechanically ventilating said patient to provide oxygen during said sedating step.

12. The therapy of claim 11 further comprising paralyzing said patient with a neuromuscular blocking agent to minimize vomiting.

13. The therapy of claim 9 wherein said sedating step comprises administering 2, 6-diisopropylphenol.

14. The therapy of claim 13 wherein said administering step is accomplished within about 3 hours.

15. A narcotic detoxification therapy, comprising:
   sedating a patient having an opioid addiction with 2,6-diisopropylphenol;
   administering a diarrhea suppressant containing octreotide acetate;
   intubating and mechanically ventilating said patient during said sedating step; and
   intravenously administering naloxone hydrochloride to initiate opioid withdrawal in said patient, whereby said patient remembers little of a plurality of symptoms of said withdrawal and can be released within eight hours of beginning said therapy without experiencing significant diarrhea.

16. A method of detoxifying a patient addicted to one or more opioids, comprising:
   sedating said patient with an anesthetic agent;
   administering to said patient a diarrhea suppressant;
   detoxifying said patient by injecting an opioid antagonist into said patient;
   reviving said patient from the effects of said anesthetic agents,
   whereby said patient can be discharged in an ambulatory condition within about eight hours of being sedated with said anesthetic agent without a significant amount of diarrhea; and
   administering antagonist maintenance therapy to said patient by a time-releasable subcutaneously implanted antagonist.

17. The method of claim 16 wherein said detoxifying step is accomplished within about four hours, and said antagonist maintenance therapy is conducted with naltrexone to release a therapeutic dosage thereof for at least one week.

18. The method of claim 16 wherein said anesthetic agent comprises 2,6-diisopropylphenol.

19. The method of claim 16 wherein said opioid antagonist comprises 17-allyl-4, 5 α epoxy-3, 14-dihydroxymorphinan-6-one hydrochloride.

20. The method of claim 16 wherein said diarrhea suppressant comprises octreotide acetate.

21. The method of claim 20 further comprising intubating said patient in order to minimize aspiration of vomitus.

22. The method of claim 20 further comprising paralyzing said patient with a neuromuscular blocking agent.

23. An opioid detoxification therapy, comprising:
   sedating a patient addicted to an opiate by administering a rapid acting intravenous, anesthetic agent;
   administering a diarrhea suppressant containing an octapeptide with pharmacologic actions mimicking those of a natural hormone, somatostatin, intravenously administering a narcotic antagonist containing naloxone hydrochloride to said patient while said patient is sedated to induce withdrawal;

and reviving said patient by at least terminating an intravenous delivery of said anesthetic agent, whereby said patient remembers little of a plurality of symptoms associated with said withdrawal and experiences little or no diarrhea; and administering antagonist maintenance therapy to said patient by a time-releasable subcutaneously implanted antagonist.

24. The therapy of claim 23 wherein said narcotic antagonist comprises 17-allyl-4, 5 α epoxy-3, 14-dihydroxymorphinan-6-one hydrochloride.

25. The therapy of claim 23 further comprising mechanically ventilating said patient to provide oxygen during said sedating step.

26. The therapy of claim 25 further comprising paralyzing said patient with a neuromuscular blocking agent to minimize vomiting.

27. The therapy of claim 22 wherein said sedating step comprises administering 2, 6-diisopropylphenol.

28. The therapy of claim 27 wherein said administering step is accomplished within about 3 hours.

29. A narcotic detoxification therapy, comprising:

sedating a patient having an opioid addiction with 2,6-diisopropylphenol;

administering a diarrhea suppressant containing octreotide acetate;

intubating and mechanically ventilating said patient during said sedating step; and intravenously administering naloxone hydrochloride to initiate opioid withdrawal in said patient, whereby said patient remembers little of a plurality of symptoms of said withdrawal and can be released within eight hours of beginning said therapy without experiencing significant diarrhea; and followed by administering antagonist maintenance therapy to said patient by a time-releasable subcutaneously implanted antagonist.

\* \* \* \* \*